(12) United States Patent
Moser

(10) Patent No.: US 8,343,103 B2
(45) Date of Patent: Jan. 1, 2013

(54) INJECTION DEVICE WITH TENSIONING SPRING AND TENSIONING ELEMENT

(75) Inventor: Ulrich Moser, Heimiswil (CH)

(73) Assignee: TecPharma Licensing AG, Burgdorf (CH)

(*) Notice: Subject to any disclaimer, the term of this patent is extended or adjusted under 35 U.S.C. 154(b) by 42 days.

(21) Appl. No.: 12/249,069

(22) Filed: Oct. 10, 2008

(65) Prior Publication Data
US 2009/0259181 A1 Oct. 15, 2009

Related U.S. Application Data

(63) Continuation of application No. PCT/CH2007/000177, filed on Apr. 12, 2007.

(30) Foreign Application Priority Data

Apr. 12, 2006 (DE) .......................... 10 2006 017 209

(51) Int. Cl.
*A61M 5/20* (2006.01)
(52) U.S. Cl. .......................... 604/135; 604/134; 604/157
(58) Field of Classification Search .......... 604/131–137, 604/157, 204–207
See application file for complete search history.

(56) References Cited

U.S. PATENT DOCUMENTS

| 2,392,196 | A | | 1/1946 | Smith |
| 4,258,713 | A | * | 3/1981 | Wardlaw ...................... 604/139 |
| 5,092,842 | A | * | 3/1992 | Bechtold et al. ............. 604/135 |
| 5,104,380 | A | | 4/1992 | Holman et al. |
| 6,620,137 | B2 | * | 9/2003 | Kirchhofer et al. .......... 604/218 |
| 2005/0049550 | A1 | | 3/2005 | Kirchhofer et al. |

FOREIGN PATENT DOCUMENTS

| EP | 0943349 A1 | 9/1999 |
| EP | 1759728 A1 | 3/2007 |
| FR | 2728172 A1 | 6/1996 |

* cited by examiner

*Primary Examiner* — Nicholas Lucchesi
*Assistant Examiner* — Rebecca E Eisenberg
(74) *Attorney, Agent, or Firm* — Dorsey & Whitney LLP; David E. Bruhn, Esq.

(57) ABSTRACT

An injection device including a receiving device movable in an insertion movement relative to the injection device, a tensioning element, e.g. a spring, which bears on a part of the injection device, and a coupling element for coupling the receiving device to the spring such that, during an insertion movement of the receiving device the spring is tensioned. In some embodiments, the invention encompasses a method for preparing an injection device for dispensing a substance from an ampoule, wherein a discharging spring of the injection device is tensioned by introduction of the ampoule into the injection device.

22 Claims, 3 Drawing Sheets

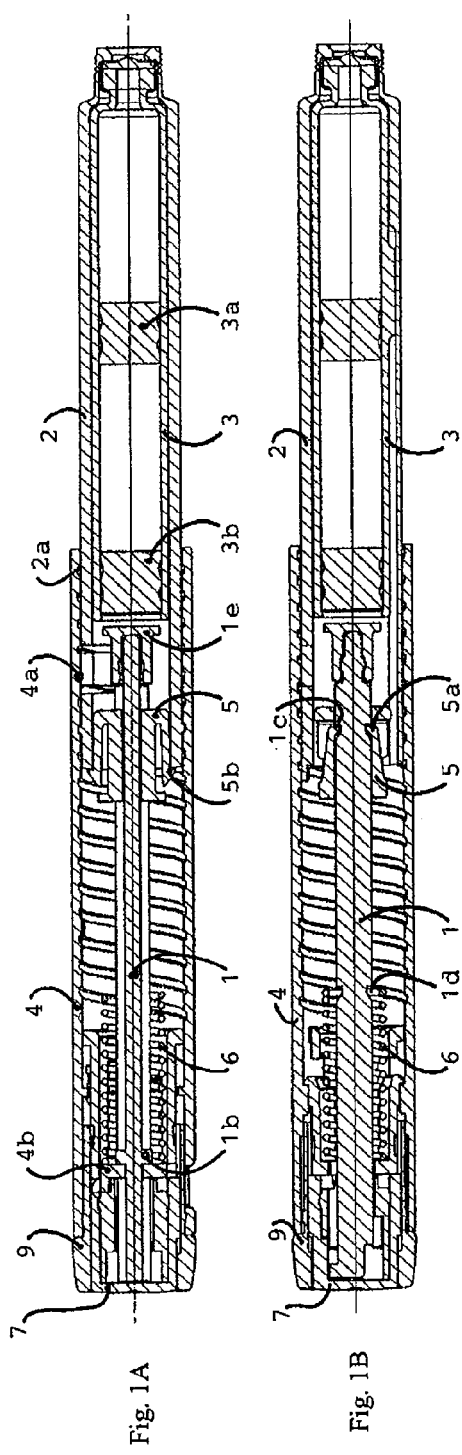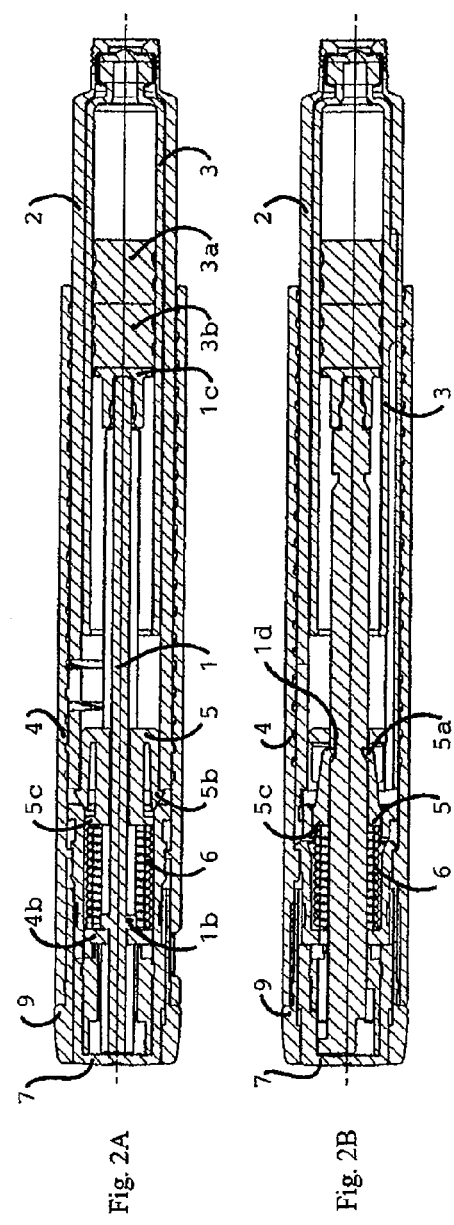
Fig. 1A  Fig. 1B  Fig. 2A  Fig. 2B

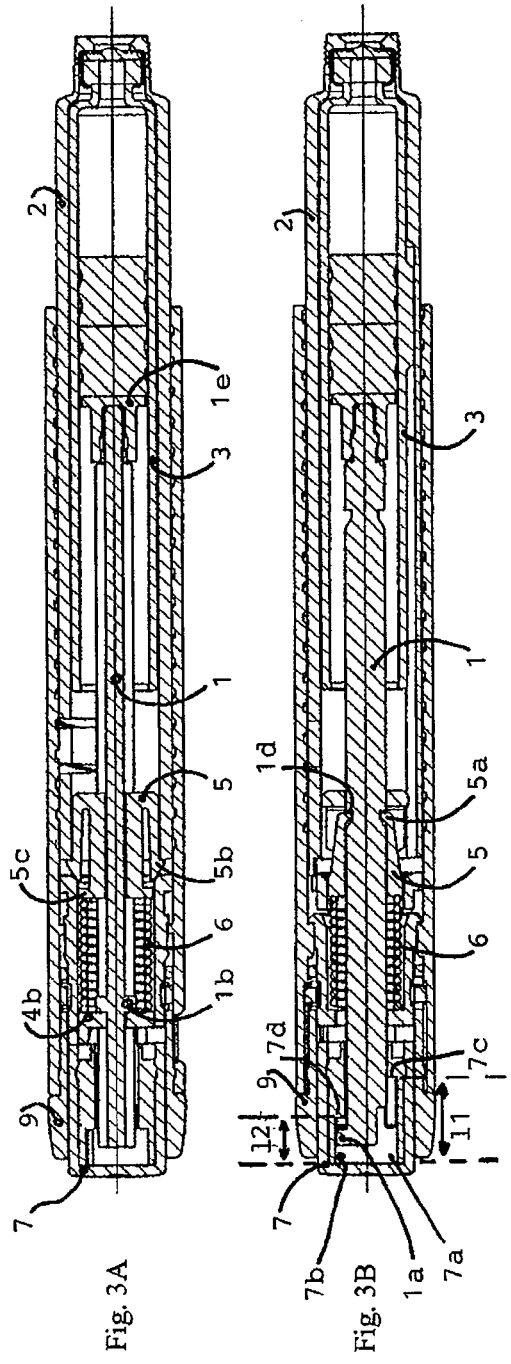
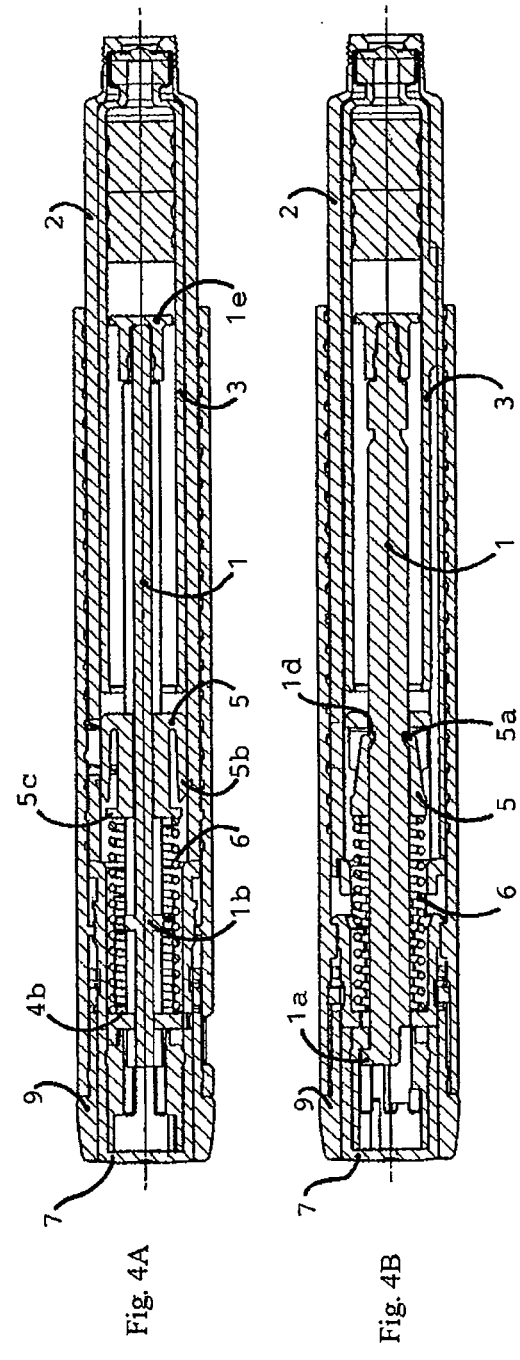
Fig. 3A  Fig. 3B  Fig. 4A  Fig. 4B

INJECTION DEVICE WITH TENSIONING SPRING AND TENSIONING ELEMENT

CROSS-REFERENCE TO RELATED APPLICATIONS

This application is a continuation of International Patent Application No. PCT/CH2007/000177 filed Apr. 12, 2007, and claims priority to German Application No. DE 10 2006 017 209.4 filed Apr. 12, 2006, the entire contents of both of which are incorporated herein by reference.

BACKGROUND

The present invention relates to devices for injecting, dispensing, administering, infusing or delivering a substance, and to methods of making and using such devices. More particularly, it relates to a device for dispensing a substance, e.g. an injection device or an injection pen, which has a spring for administering a measured dose of an injectable product or substance from an ampoule, a double-chamber ampoule, for example. Some embodiments of such a device may be used for self-administering the product or substance. In some embodiments, the device may take the form of a disposable injection device or injector, in others, an automatic injection device or automatic injection pen.

U.S. Pat. No. 5,104,380 discloses an injection device wherein the injection needle is fitted on the device manually and the subsequent dispensing of an active substance from the device takes place automatically by a drive. The drive is provided in the form of a spring, which is tensioned by a movement of a dose setting element to set a desired dose to be administered. The spring is blocked or locked in the tensed state until activated. Upon activation, it automatically drives a dispensing mechanism, which drives or moves the active substance through the injection needle.

SUMMARY

One object of embodiments of the present invention is to provide an injection device and a method of preparing an injection device which simplify handling of such injection devices.

Thus, in one embodiment, the present invention comprises an injection device comprising a plunger rod, a container for a substance to be dispensed, wherein the container is able to be inserted in the injection device and, after being inserted, is able to move relative to the injection device, a dispensing spring supported on a part of the injection device, and a coupling element for coupling the container with the dispensing spring so that the spring is tensioned when the container is inserted, the tensioned spring acting on the plunger rod to cause an amount of the substance to be dispensed.

In one embodiment, the present invention comprises an injection device including a receiving device movable in an insertion movement relative to the injection device, a tensioning element, e.g. a spring, which bears on a part of the injection device, and a coupling element for coupling the receiving device to the spring such that, during an insertion movement of the receiving device the spring is tensioned. In some embodiments, the invention encompasses a method for preparing an injection device for dispensing a substance from an ampoule, wherein a discharging spring of the injection device is tensioned by introduction of the ampoule into the injection device.

In one embodiment, the present invention relates to an injection device with a receiving device for a substance to be dispensed, in particular with an ampoule holder, which is movable relative to the injection device or a part thereof, with a tensioning element, in particular a spring, which can bear on a part of the injection device, and with a coupling element for coupling the receiving device to the spring such that, during an insertion movement of the receiving device into the injection device, the spring can be tensioned. The invention also relates to a method for preparing an injection device for dispensing a substance from an ampoule, wherein a discharging spring of the injection device is tensioned by introduction of the ampoule into the injection device In one embodiment, an injection device in accordance with the present invention comprises a holder device for a substance to be administered, in which the substance to be administered can be either introduced, housed directly or contained, for example in a single-chamber or double-chamber ampoule, in which case the holder device will be designed as an ampoule holder. The holder device can be moved relative to the injection device, e.g., relative to a housing portion of an injection pen. In some embodiments, an element of the injection device serving as the holder or the ampoule holder, for example, can be pushed or screwed into the injection device or into a part of it, for example into the housing of the injection device. If using a known double-chamber ampoule, the substances contained in the double-chamber ampoule can be mixed during the pushing or screwing operation and are thus prepared for administering to a patient.

In some embodiments, a tensioning element is disposed on or in the injection device. The tensioning element may be a suitable spring supported at one end against an element in or on the injection device or on its housing, such as a ring or a disc provided for this purpose. In some embodiments, the tensioning element can be tensioned in the direction pointing away from the supported end or surface by a tensioning or coupling element which can be connected to or coupled with the holder device, e.g. the ampoule holder, as an ampoule is introduced and/or the holder device is pushed in or screwed in.

In some embodiments, tensioned by introducing an ampoule in accordance with the present invention, the spring may be held in the tensioned state by a coupling element which may be provided in the form of a sliding sleeve or stroke sleeve, until the coupling element, which maintains the spring tension due to a coupling with the ampoule housing, is uncoupled from the ampoule housing by operating a trigger or actuator, thereby enabling the spring to relax. The spring may act on a plunger rod, part of the mechanism that enables an injection or dispensing, directly or via the coupling element, and can push it in the distal direction so that one or more stoppers are pushed into the ampoule by a movement of the plunger rod in the distal direction, thereby forcing or urging a substance out of the ampoule and dispensing it for the injection.

In some embodiments, the coupling element may be integrated in the holder device or ampoule holder, connected to it, mounted on it or secured to it by a releasable connection, such as a retaining or catch element. In some embodiments, the coupling element is not coupled with the ampoule holder until the ampoule holder has been inserted and/or moved. For example, the coupling element may have at least one and, in some preferred embodiments, two or more retaining or catch elements, to permit an operable coupling or connection with or between the ampoule holder and/or the plunger rod. To this end, the retaining or catch elements may be biased radially inwardly and/or outwardly and, in the case of a cylindrical or sleeve-shaped coupling element pushed inwardly, in a direction toward the plunger rod, and/or outwardly in the direction of a housing or housing portion of the injection device.

In some embodiments, the one or more retaining or catch elements may have oblique surfaces or part-pieces which are not perpendicular to the longitudinal axis of the injection device or, in other words, which converge in a conical arrangement. A member pushing on the coupling element in the axial direction of the injection device, such as an element connected to a trigger button or setting ring, releases a retaining or catch element holding the coupling element in an axially fixed position from a coupling or catch connection with the housing of the injection device to release the coupling element. The coupling element is moved by the pressure of the spring as it is biased in the distal direction of the injection device when the ampoule is being pushed on. This pushing movement of the coupling element can be transmitted to the plunger rod via a coupling or catch connection.

In some embodiments, the coupling element is mounted so that it is prevented from rotating on the plunger rod. For example, the plunger rod may have a non-round profile, e.g. a rectangular or square cross-section, in which case the coupling element may be sleeve shaped and may have a guide region in which the plunger rod is guided as it slides axially so that the coupling element can be moved along the plunger rod in the axial direction. A groove or web may also be provided in or on the plunger rod in the longitudinal direction, in which case a co-operating complementary element may be provided on the coupling element, e.g. a suitable web or a groove.

In some preferred embodiments, the ampoule holder is connected to the injection device or a housing thereof by a thread or threads so that the ampoule holder can be screwed into the injection device. The ampoule holder has an external thread, which can be turned in an internal thread of the injection device. Another option would be to push or slide the ampoule holder into the injection device without any relative rotating movement.

In some embodiments, a dose setting ring is provided on the injection device to set or select the dose to be dispensed. In some embodiments, the dose setting ring is blocked or locked, i.e. can not be rotated relative to the injection device or can be rotated only to a very limited degree, until an ampoule has been fully inserted. To this end, one or more stops are provided on the dose setting ring, which are able to move unhindered when the ampoule holder is in the inserted state. The stops run or extend at least partially inside a groove, e.g. an annular groove. The groove may be provided in a functional sleeve disposed in the interior of the housing. In the state in which the ampoule holder has not been inserted, the stops lie opposite one or more complementary stops so that their movement is blocked or prevented. The complementary stops may be moved out of the path of movement of the stops of the dose setting ring by inserting the ampoule holder so that the dose setting ring can be freely rotated to set the dose. To this end, the functional sleeve can be pushed relative to the dose setting ring as a whole or the functional sleeve may be split so that only a part of the functional sleeve slides as the ampoule holder is inserted so that complementary stops are moved out of the annular groove.

In some embodiments, the trigger button for actuating the dispensing operation is coupled with the dose setting ring so that when setting a dose by using the setting ring, the trigger button is moved out of the housing of the injection device. To this end, a thread-type coupling may be provided between the trigger button and setting ring, so that a trigger button mounted so that it can not rotate and is moved out of the injection device due to a rotation of the setting ring.

In one embodiment, the trigger button is prevented from rotating but is mounted so that it can be moved axially on the dose setting ring. Due to the rotating movement of the dose setting ring, the trigger button can be moved axially relative to the dose setting ring along a guide arrangement. A suitable guide arrangement might be provided by mutually adapted oblique surfaces on the trigger button and an element which is prevented from rotating relative to the dose setting ring. The trigger button is recessed so far into the housing or into the dose setting ring that it is inaccessible until it has been activated by inserting the ampoule holder or turning the dose setting ring.

When the setting operation has been completed, the trigger button is extended in a position in which it can be activated. Dispensing can be triggered by operating, e.g. pushing or touching, the trigger button. In this respect, the trigger button is moved back to or into a recessed position in which it inaccessible for further operation. In one preferred embodiment, the dose setting ring is also returned to a blocked or locked position once the substance has been dispensed, i.e. when the trigger button has been operated. The injection device is then completely locked to prevent further operation after performing one dispensing operation. It is then not possible to set another dose or operate the trigger button again. The injection device, e.g. pen, is fully locked.

In some embodiments, the invention comprises a method of preparing an injection device for dispensing a substance from an ampoule, whereby a spring contained in the injection device is tensioned by pushing an ampoule or an ampoule holder relative to, e.g. into, the injection device or its housing. An injection takes place due to the fact that the tensed spring is relaxed after a trigger or actuating button has been operated and a force is exerted on a plunger rod which pushes into the ampoule.

BRIEF DESCRIPTION OF THE DRAWINGS

FIGS. 1A and 1B are longitudinal sectional views of an embodiment of an injection device in accordance with the present invention with a dispensing spring, wherein the spring is relaxed before an ampoule is screwed into the device;

FIGS. 2A and 2B are longitudinal sectional views showing an embodiment of an injection device in accordance with the present invention after an ampoule has been screwed into the device, the dispensing spring being tensed;

FIGS. 3A and 3B are longitudinal sectional views showing an embodiment of an injection device in accordance with the present invention after a dose has been set by using a setting ring, with the trigger button extracted.

FIGS. 4A and 4B are longitudinal sectional views showing an embodiment of an injection device in accordance with the present invention in n end position after pressing in the trigger button and releasing the spring to dispense a dose;

DETAILED DESCRIPTION

With regard to fastening, mounting, attaching or connecting components of embodiments of the present invention, unless specifically described otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or its components may be selected from appropriate materials such as metal, metallic alloys, ceramics, plastics, etc.

Figure 1C:
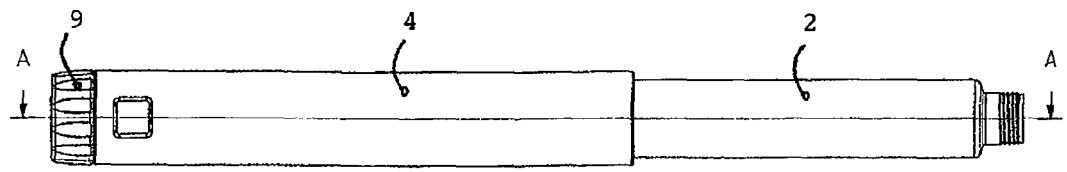
FIGS. 1C and 1D are side views, perpendicular to one another, showing the injection device illustrated in FIGS. 1A and 1B.

FIG. 1A is a cross-section in the longitudinal direction of an embodiment of an injection device in accordance with the present invention, also illustrated in FIG. 1C, with an ampoule holder 2 in which an ampoule 3 is inserted, partially screwed into an internal thread 4a of the housing 4 of the injection device by using the external thread 2a of the ampoule holder 2. The ampoule 3 is a double-chamber ampoule and has two stoppers 3a and 3b, which close off two substances in the ampoule 3 which have to be mixed and are separated from one another in an initial position. In the axial direction, a plunger rod 1 is locked by a ring 1b projecting radially out from the plunger rod 1 to prevent it from moving in the proximal direction. The ring lies against a passage orifice formed by webs 4b, the passage orifice being smaller than the external diameter of the ring 1b. A sliding sleeve or stroke sleeve 5 is disposed on the plunger rod 1 so that it is prevented from rotating but is able to slide on the plunger rod 1.

Figure 1D:

FIG. 1B is a cross-section illustrating the device shown in FIG. 1A in section through a plane illustrated in FIG. 1D, which is perpendicular to the plane shown in section in FIG. 1A. The sliding sleeve 5 has catch elements 5a biased radially inwardly, which locate in recesses 1c of the plunger rod 1 and are thus relaxed in an initial position. A spring 6 is supported against a contact surface 4b in the interior of the injection device and is relaxed in the position illustrated in FIGS. 1A-D.

When the ampoule holder 2 is turned into the housing 4, the rear stopper 3b of the ampoule 3 comes into contact with a contact element 1e of the plunger rod 1. When the ampoule holder 2 is turned further relative to the ampoule 3, the substances contained in the double-chamber ampoule 3 are mixed.

Figure 2C:
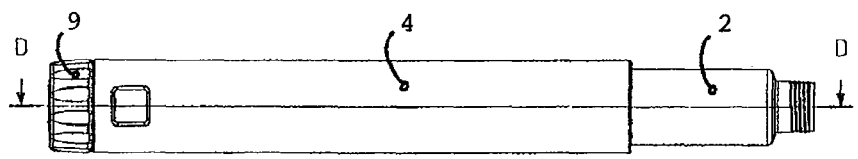
FIGS. 2C and 2D are side views, perpendicular to one another, showing the injection device illustrated in FIGS. 2A and 2B.
Figure 2D:
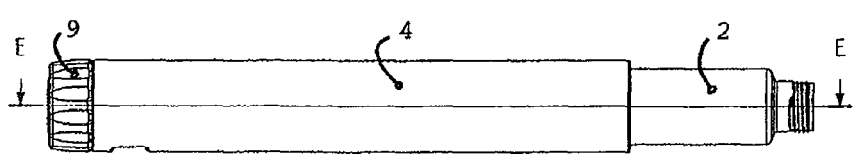

FIG. 2A, and FIGS. 2C and 2D, illustrates the injection device shown in FIG. 1A after screwing the ampoule holder 2 into the housing 4. The sliding sleeve 5, which is coupled with the ampoule holder 2 by retaining elements 5b biased radially outwardly, was pushed in the proximal (rearward) direction of the injection device due to the screwing-in movement of the ampoule holder 2. It therefore causes the spring 6 to be tensioned between the contact surfaces 4b and 5c. In some embodiments, the spring is in contact with the proximal surface 5c of the sliding sleeve 5 during the ampoule screwing-in movement, or part of it, and is compressed by the sliding sleeve 5 and thus tensioned. The locating elements 5a of the sliding sleeve 5 biased radially inwardly are pulled out of the recesses 1c of the plunger rod 1 and locate in or move into the rear recesses 1d of the plunger rod 1 in the position illustrated in FIG. 2B.

Before the ampoule holder 2 is screwed in, the dose setting ring is not able to rotate relative to the housing 4. To this end, the dose setting ring has stops, which are provided on flexible arms disposed in the circumferential direction. The stops move opposite an annular groove disposed in a functional sleeve. During a dose setting movement, the stops are pushed into the annular groove due to a movement of the flexible arms because teeth are provided opposite to the arms, along which the arms are moved, generating an audible clicking noise. As the flexible arms run across the teeth, they are pushed into the annular groove by each tooth. The functional sleeve is prevented from rotating relative to the housing and is of a two-part design, which two parts are able to slide telescopically relative to one another. When the parts of the functional sleeve are in the state extracted from one another, complementary stops move so that they lie inside the annular groove and sit opposite the stops on the dose setting ring, blocking or locking the dose setting ring to prevent it from rotating. When the parts of the functional sleeve are in the state in which they are axially pushed together, the complementary stops move so that they lie outside the track of the annular groove so that the dose setting ring can be rotated. The parts of the functional sleeve are pushed together by screwing in the ampoule holder 2. The dose setting ring can therefore not be rotated until the ampoule holder 2 has been inserted.

Figure 3C:
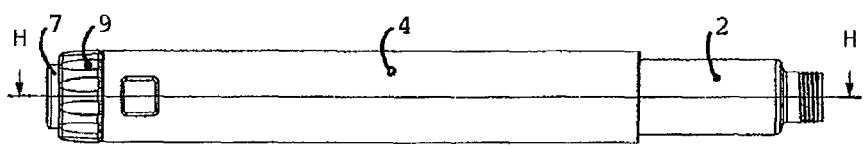
FIGS. 3C and 3D are side views, perpendicular to one another, showing the injection device illustrated in FIGS. 3A and 3B.
Figure 3D:
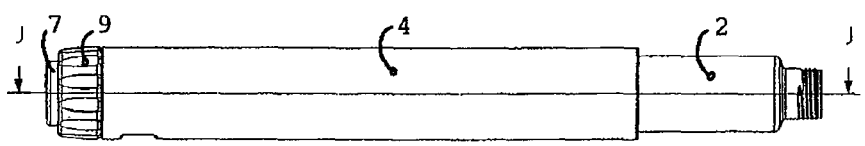

FIG. 3A, and FIGS. 3C and 3D, illustrates the injection device illustrated in 2A after the setting ring 9 has been rotated to set or select a dose and the trigger button 7 has been extracted or extended from the injection device by a guiding action due to the setting movement of the setting ring 9. To this end, a proximally extending projection with an oblique surface is provided on a proximal end face of the functional sleeve. A distally (forwardly) extending projection with an oblique surface is provided on a distal end face of the trigger button, which complements the surface of the functional sleeve. As the dose setting ring is turned, the trigger button is driven with it and rotated relative to the functional sleeve, and the oblique surfaces slide off one another and thus push the trigger button axially relative to the functional sleeve and the dose setting ring. The trigger button is transferred from a recessed state into an operable state as a result.

When the trigger button is pushed into the injection device, the functional sleeve acts on the sliding element 5 and releases the spring. This being the case, the functional sleeve therefore acts as a releasing element 8.

Grooves of differing axial lengths 11 and 12 are provided on the internal face of the trigger button 7, as illustrated by the grooves 7a and 7b in FIG. 3B, which fix the maximum possible axial movement of the plunger rod 1. The rod 1 has a lug 1a at its proximal end, which moves against a stop 7c or 7d bounding the respective grooves 7a, 7b once the plunger rod 1 biased by the spring 6 has been released, thereby fixing the maximum possible dose which can be dispensed.

Figure 4C:
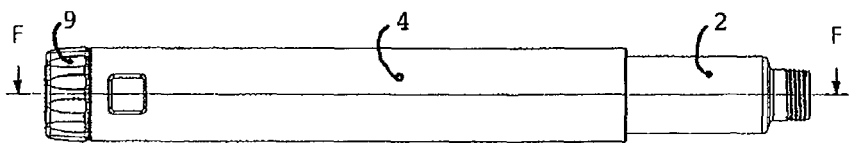
FIGS. 4C and 4D are side views, perpendicular to one another, showing the injection device illustrated in FIGS. 4A and 4B.
Figure 4D:
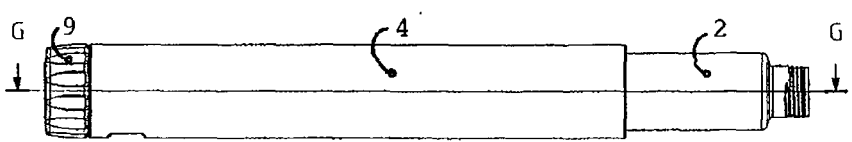

When the trigger button 7 is pushed into the injection device as illustrated in FIG. 4A, and FIGS. 4C and 4D, the retaining element 5b biased radially outwardly holding the sliding sleeve 5 on the proximal end of the ampoule holder 2, by which the releasing element 8 co-operating with the button 7 pushes against an oblique surface 5c of the retaining element 5b and thus pushes it radially inwardly, is released from its engagement with the ampoule holder 2 so that the sliding sleeve 5 is no longer locked relative to the injection device in the axial direction. The spring 6 pushing on the sliding sleeve 5 pushes the sliding sleeve 5 in the distal (forward) direction. Since the sliding sleeve 5 drives the plunger rod 1 with it by the catch elements 5a biased radially inwardly and locating in the recesses 1d of the plunger rod 1, the plunger rod 1 is pushed into the ampoule 3 and thus pushes on the rear stopper 3b, thereby causing the mixed substance contained in the ampoule 3 to be dispensed.

In the position illustrated in FIG. 4B, after the dose has been dispensed from the ampoule 3, the trigger button 7 is held in the injection device by the lug 1a of the plunger rod 1 and can no longer be pulled out, so that the injection device can no longer be used for another injection.

Embodiments of the present invention, including preferred embodiments, have been presented for the purpose of illustration and description. They are not intended to be exhaustive or to limit the present invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device comprising a housing, a plunger rod, a container for a substance to be dispensed, wherein the container is manually inserted in the injection device by a user prior to dispensing, said manual insertion including moving the container relative to the injection device and the housing and, after being inserted, the container is moveable relative to the injection device, a dispensing spring supported on a part of the injection device, and a coupling element for coupling the container with the dispensing spring so that the dispensing spring is tensioned simultaneously by and with the manual insertion movement of the container, wherein, after the insertion movement of the container, the tensioned dispensing spring moves the plunger rod to cause an amount of the substance to be dispensed.

2. The injection device as claimed in claim 1, wherein the coupling element further comprises a catch element and the plunger rod further comprises a first recess and a second recess, wherein the catch element connects the coupling element to the first recess in a relaxed position of the dispensing spring prior to insertion of the holder device, and wherein the catch element connects the coupling element to the second recess in a tensed position of the dispensing spring after insertion of the holder device.

3. An injection device comprising a housing, a holder device for a substance to be dispensed, the holder device able to move relative to the injection device or a part thereof, a dispensing spring supported on a part of the injection device and a coupling element for coupling the holder device with the dispensing spring, wherein a user manually inserts the holder device into the injection device and during the manual insertion the holder device is moved relative to the injection device and the housing and the dispensing spring is simultaneously tensioned, which tensed dispensing spring subsequently moves a plunger rod of the injection device to dispense the substance.

4. The injection device as claimed in claim 3, wherein the coupling element is sleeve-shaped.

5. The injection device as claimed in claim 3, wherein the coupling element comprises a catch element to connect the coupling element to a recess on the plunger rod, wherein the catch element locates in the recess upon tensioning the spring.

6. The injection device as claimed in claim 3, wherein the coupling element comprises a retaining element, said retaining element coupling to and slaved by the holder device when the holder device is introduced into the injection device, wherein the tensed spring is held in a tensed state between an injection device housing and the coupling element by the retaining element.

7. The injection device as claimed in claim 5, wherein the coupling element is mounted on the plunger rod so that the coupling element is prevented from rotating.

8. The injection device as claimed in claim 6, wherein the retaining element further comprises an obliquely extending surface, and upon triggering the injection device, the retaining element is moved radially via a movement of the obliquely extending surface away from the holder device to release the retaining element from holding the tensed spring in the tensed state.

9. The injection device as claimed in claim 8, wherein the coupling element further comprises a catch element to connect the coupling element to a recess on the plunger rod, said catch element locating in the recess upon tensioning the spring, wherein upon triggering the injection device, the dispensing spring pushes on the coupling element in a dispensing direction and the coupling element carries the plunger rod via the catch element located in the recess in order to dispense the substance.

10. The injection device as claimed in claim 9, further comprising a trigger button for triggering the injection device, wherein upon dispensing the substance, the trigger button is held in the injection device by the plunger rod, such that the trigger button is prevented from triggering.

11. The injection device as claimed in claim 3, wherein the holder device is coupled with the injection device by a thread.

12. The injection device as claimed in claim 3, wherein the holder device is an ampoule holder.

13. The injection device as claimed in claim 12, further comprising a dose setting ring which is locked until the ampoule has been fully inserted, wherein upon full insertion of the ampoule, the dose setting ring is unlocked and is moved by the user to set a dose.

14. The injection device as claimed in claim 13, further comprising a trigger, wherein the trigger is extended from the injection device by the movement of the setting ring.

15. The injection device as claimed in claim 3, wherein the coupling element is provided as a slidable sleeve disposed on the plunger rod, and wherein as the holder device is introduced into the injection device, the coupling element is slaved by the holder device and slides along the plunger rod in the direction opposite the dispensing direction to tense the dispensing spring.

16. The injection device as claimed in claim 15, wherein the coupling element comprises a catch element that locates in a recess on the plunger rod upon tensing the dispensing spring and holds the dispensing spring in a tensed state.

17. The injection device as claimed in claim 16, wherein the coupling element comprises a retaining element that couples with the holder device such that the coupling element is held on the plunger rod and the holder device in the tensed state.

18. The injection device as claimed in claim 17, wherein upon triggering the injection device, the retaining element uncouples from the holder device such that the dispensing spring is released from the tensed state and moves the coupling element and the plunger rod coupled to the coupling element by the catch element located in the recess.

19. The injection device as claimed in claim 3, wherein the plunger rod is locked against moving in a direction opposite the dispensing direction during introduction of the holder device and mixes a dual chamber ampoule arranged in the holder device as the dispensing spring is tensed.

20. The injection device as claimed in claim 3, wherein the coupling element further comprises a catch element and the plunger rod further comprises a first recess and a second recess, wherein the catch element connects the coupling element to the first recess in a relaxed position of the dispensing spring prior to insertion of the holder device, and wherein the catch element connects the coupling element to the second recess in a tensed position of the dispensing spring after insertion of the holder device.

21. A method of preparing an injection device for dispensing a substance from an ampoule, the method including the step of tensioning a dispensing spring of the injection device during a user of the device manually introducing an end of the ampoule, opposite a dispensing end of the ampoule, into the injection device.

22. The method of claim 21, further comprising releasing the tensed dispensing spring by actuating a triggering button of the injection device, wherein the released dispensing spring relaxes and delivers the substance from the dispensing end of the ampoule.

* * * * *